(12) United States Patent
Stibelli et al.

(10) Patent No.: US 8,304,186 B2
(45) Date of Patent: Nov. 6, 2012

(54) REACTOR FOR PERFORMING BIOCHEMICAL PROCESSES

(75) Inventors: Sergio Stibelli, Trieste (IT); Niccolo Di Pietro, Lammari (IT)

(73) Assignees: Smart Hospital S.R.L., Freddana (IT); Genedia S.R.L., Lammari (IT); Talent S.R.L., Trieste (IT)

( * ) Notice: Subject to any disclaimer, the term of this patent is extended or adjusted under 35 U.S.C. 154(b) by 308 days.

(21) Appl. No.: 12/516,228

(22) PCT Filed: Nov. 16, 2007

(86) PCT No.: PCT/EP2007/009937
§ 371 (c)(1),
(2), (4) Date: Jun. 22, 2009

(87) PCT Pub. No.: WO2008/064783
PCT Pub. Date: Jun. 5, 2008

(65) Prior Publication Data
US 2010/0055698 A1    Mar. 4, 2010

(30) Foreign Application Priority Data
Nov. 27, 2006 (IT) .......................... M12006A002272

(51) Int. Cl.
*C12Q 1/68* (2006.01)
*C12M 1/00* (2006.01)
*C07H 21/00* (2006.01)

(52) U.S. Cl. ..................... 435/6.1; 435/283.1; 536/22.1; 536/25.4

(58) Field of Classification Search ........... 435/6, 283.1, 435/6.1; 536/22.1, 25.4
See application file for complete search history.

(56) References Cited

U.S. PATENT DOCUMENTS

| 5,364,591 | A | 11/1994 | Green et al. |
| 5,436,328 | A | 7/1995 | Malmquist |
| 6,281,008 | B1 * | 8/2001 | Komai et al. ............... 435/306.1 |
| 7,947,450 | B2 * | 5/2011 | Stordeur et al. ............. 435/6.14 |
| 2002/0042125 | A1 * | 4/2002 | Petersen et al. ............ 435/287.2 |
| 2004/0126796 | A1 * | 7/2004 | Carlson et al. ..................... 435/6 |
| 2006/0011539 | A1 | 1/2006 | Lee et al. |
| 2006/0084185 | A1 * | 4/2006 | Landers et al. ............... 436/177 |
| 2007/0071637 | A1 * | 3/2007 | Numajiri ......................... 422/57 |
| 2010/0248213 | A1 * | 9/2010 | Feiglin .............................. 435/5 |

FOREIGN PATENT DOCUMENTS
WO           02058845       8/2002
WO   WO2004/047992   *   6/2004

* cited by examiner

*Primary Examiner* — Ethan C Whisenant
(74) *Attorney, Agent, or Firm* — Dennison, Schultz & MacDonald

(57) ABSTRACT

A reactor (1) for performing biochemical processes, particularly for extraction, purification, enrichment, sedimentation, comprising a container which is provided with at least one mouth (2) which is associated with closure means (3) of the removable type, the container having internally at least one process compartment (4), adapted to accommodate a sample of biochemical material to be processed, at least one containment chamber (5) for a process agent, and at least first means for transferring the process agent from the containment chamber to the process compartment.

30 Claims, 7 Drawing Sheets

REACTOR FOR PERFORMING BIOCHEMICAL PROCESSES

TECHNICAL FIELD

The present invention relates to a reactor for performing biochemical processes, particularly for extraction, purification, enrichment and sedimentation.

BACKGROUND ART

Several biochemical processes are known, such as for example extraction and purification of nucleic acids (DNA, RNA), viral enrichment, subparticle enrichment or sedimentation and purification of proteins, which are performed by means of a sequence of one or more steps, among which the following are mentioned merely by way of example: mixing of a sample with one or more agents, lysis of biological material, sedimentation, separation by centrifugation, removal of waste fractions of the process, washing with suitable agents, and others.

These processes are performed within reactors or test tubes which are typically constituted by a cylindrical vessel which is closed at the bottom and provided with an upper opening with which a closure stopper is detachably associated.

To perform the different steps, in particular the steps which provide for the addition of process agents (lysis agents, washing agents, or others) or the removal of waste fractions, it is necessary to remove the closure stopper and then reapply it.

Moreover, if these addition or removal steps are separated by centrifugation steps, it is also necessary to remove the reactors from the centrifugation device.

These known reactors suffer drawbacks, among which mention is made of the fact that they require the execution of successive handling, opening and closure operations, which in addition to being awkward entail an onerous expenditure of time and costs.

Another drawback of known reactors consists in that particularly if the biochemical processes are performed manually, they entail high safety risks for the assigned personnel. Considering the fact that the processed biological material often contains infectious or pathogenic agents, the successive operations for handling, opening and closing known reactors in fact entail risks of infection of assigned personnel or of sample contamination, a phenomenon known as "carry over".

Another disadvantage consists in that the automation of the biochemical processes performed in reactors of the known type requires the use of tools, such as handling robots, which are structurally and constructively complicated, require the assistance of complex and expensive management and control apparatuses, and require frequent maintenance.

With particular reference to the extraction and purification of nucleic acids (DNA-RNA), different processes are known which can be divided into processes based on the use of so-called "magnetic beads" and processes based on the use of filters.

In processes based on the use of magnetic beads, separation of the nucleic acids from the sample is achieved by using magnetic particles made of iron and coated with silica. These particles are dispersed in a reactor which contains an aqueous solution of nucleic acid. The nucleic acid adheres to the outer surface of the particles, forming hydrogen bonds. A magnetic field is then applied to the outside of the container so as to convey the particles, with the nucleic acid adhered thereto, to a preset region of such reactor, so as to allow removal of the aqueous solution and execution of the necessary washes without losing the particles with the nucleic acid adhered thereto. The nucleic acid thus separated is then eluted.

In processes based on the use of filters, separation of the nucleic acids from the sample is achieved by using silica particles to which the nucleic acid adheres with hydrogen bonds.

Both of these known processes for extracting nucleic acids suffer drawbacks, among which mention must be made of the fact that they allow to process limited volumes of samples, i.e., no more than 0.3-0.5 ml; they in fact provide for the use of commercial containers, generally plates with 48/96 wells, in which the volume per well is generally less than 2 ml.

Another drawback of these known extraction processes consists in that they do not ensure extraction of all the nucleic acid that is present in the sample due to the weakness of the hydrogen bond with which the nucleic acid adheres to the silica particles, be they magnetic or not.

Moreover, these known extraction processes are performed in known types of reactors and therefore suffer all the already-mentioned drawbacks linked to the use of such reactors.

DISCLOSURE OF THE INVENTION

The aim of the present invention is to overcome the drawbacks of known reactors with a reactor for performing biochemical processes, particularly for extraction, purification, enrichment, sedimentation, which allows to simplify the execution of the different steps in which a biochemical process is performed, such as for example: mixing a sample with one or more agents, lysis of biological material, sedimentation, separation by centrifugation, removal of waste fractions of the process, washes with suitable agents, and others.

An object of the present invention is to devise a reactor for performing biochemical processes which allows to perform safely the different steps into which a biochemical process is organized, ensuring the safety of the assigned operators and avoiding the phenomenon of so-called "carry over".

Still another object of the present invention is to devise a reactor for performing biochemical processes which allows to automate easily the different steps into which a biochemical process is organized, by using tools whose structure, manufacture and management are simple and have a low cost.

The aim of the present invention is also to provide a process for extracting nucleic acids by using a reactor according to the present invention which allows to extract nucleic acid from a biochemical sample simply and easily and allows to extract all the nucleic acid that is contained in the processed sample.

Another object of the present invention is to provide an apparatus for performing biochemical processes in an automated manner by using the reactor according to the present invention which is structurally and constructively simple and has low installation, management and maintenance costs.

Within this aim, another object of the present invention is to achieve said aim and objects with a structure which is simple, relatively easy to provide in practice, safe in use, effective in operation, and relatively low in cost.

This aim and these objects are all achieved by the present reactor for performing biochemical processes, particularly for extraction, purification, enrichment, sedimentation, characterized in that it comprises a container which is provided with at least one mouth which is associated with closure means of the removable type, said container having internally at least one process compartment, adapted to accommodate a sample of biochemical material to be processed, at least one containment chamber for a process agent, and at least first means for transferring the process agent from the containment chamber to the process compartment.

BRIEF DESCRIPTION OF THE DRAWINGS

Further characteristics and advantages of the present invention will become better apparent from the detailed description of some preferred but not exclusive embodiments of a reactor for performing biochemical processes, particularly for extraction, purification, enrichment, sedimentation, according to the invention, illustrated by way of non-limiting example in the accompanying drawings, wherein.

WAYS OF CARRYING OUT THE INVENTION

With reference to the figures, the reference numeral 1 generally designates a reactor or test tube for performing biochemical processes, particularly for extraction, purification, enrichment, sedimentation.

In the present description, the adjectives "upper" and "lower" must not be understood in a limiting sense and are understood to be referenced to the operating configuration of the reactor 1.

In the present description, the expression "process agent" is used to reference any substance or mixture of substances involved in the biochemical process, such as, merely by way of example, lysis agents, washing agents or the like.

The expression "process waste" is used to designate the fraction of the products of the biochemical process to be separated from the useful fraction, such waste being generally of the supernatant type.

The reactor 1 comprises a container provided with at least one mouth 2 which is associated with closure means constituted by a stopper 3 of the removable type, means for coupling, for example of the interlocking or bayonet type, being defined between the mouth 2 and the stopper 3.

Inside the container there are at least one process compartment 4, which is adapted to accommodate a sample of biochemical material to be processed, one or more chambers 5 for containing a process agent, and at least respective first means for transferring the process agent from the containment chamber 5 to the process compartment 4.

Moreover, inside the container there are one or more receptacles 6 for collecting the process waste and respective second means for transferring such waste from the process compartment 4 to the collection receptacle 6.

Means 7 for adjusting the first and second transfer means which can be controlled from outside are associated with the stopper 3.

The container is constituted by two elements which can be mutually associated detachably: a capsule 8 and a tubular body 9.

The capsule 8 is closed at the bottom and is provided with an upper opening 10; the process compartment 4 is defined inside the capsule 8.

The tubular body 9 has a lower end 11 which is associated detachably with the upper opening 10, for example by means of a threaded coupling; the mouth 2 which can be closed by the stopper 3 is provided at the opposite end.

The containment chamber 5, the collection receptacle 6 and the first and second transfer means are defined inside the tubular body 9.

In a preferred embodiment, the reactor 1 comprises a closure element 12 which can be associated detachably with the upper opening 10 of the capsule 8 when the latter is uncoupled from the tubular body 9.

The closure element 12 closes the capsule 8 before it is coupled to the tubular body 9 to perform the biochemical process, for example to preserve a process agent introduced beforehand in the process compartment 4.

At the end of the execution of the biochemical process, the capsule 8, inside which the product of the process accumulates, is uncoupled from the tubular body 9.

A space 13 for containing a process agent and means 14 for transferring such agent from the containment space 13 to the process compartment 4 are provided inside the closure element 12.

The tubular body 9 is provided, at its lower end 11, with a closure plate, from which two radial walls 15 protrude and delimit and separate the containment chamber 5 from the collection receptacle 6, both being connected in an upper region to the mouth 2.

A plate-like tab 16 protrudes from the lower surface of the closure plate, protrudes into the process compartment 4 and has an edge 17 which is at least partially arc-like and delimits, in cooperation with the internal surface of the process compartment 4, a region 18 for accumulating process products.

The first transfer means comprise at least one duct 19 for the rise of the agent to be transferred, which is provided, at the lower end, with an intake orifice which is accommodated within the containment chamber 5 and, at the upper end, with a discharge orifice which is connected to the process compartment 4.

In the illustrated embodiment, the riser duct 19 is provided monolithically with the stopper 3, whereas in the tubular body 9 there are a supply duct 20 which has an intake end connected, by means of a port 28 defined within the stopper 3, to the discharge orifice of the riser duct 19 and a discharge end 21 which leads into the process compartment 4.

The second transfer means comprise at least one channel 22 for the rise of the process waste, which is provided, at the lower end, with an intake hole which is accommodated within the process compartment 4 and, at the upper end, with a discharge hole which is connected to the collection receptacle 6.

The riser channel 22 extends into the tab 16 at the edge thereof which lies opposite the arc-like edge 17.

In a preferred embodiment, the riser duct 19 and/or the riser channel 22 are of the capillary type.

The means 7 for adjusting the first transfer means comprise a first intake port 23, which is provided within the stopper 3 and is connected to the containment chamber 5. The first intake port 23 is associable with means, not shown, for generating air under pressure or suction in order to produce a difference in ambient pressure between the containment chamber 5 and the process compartment 4. The resulting pressure difference is adapted to promote the transfer, through the riser duct 19 and the supply duct 20, of the process agent from the containment chamber 5 to the process compartment 4.

Likewise, the adjustment means 7 of the second transfer means comprise a second intake port 24, which is provided within the stopper 3 and is connected to the process compartment 4 through a duct 25 which is formed within the tubular body 9. The second intake port 24 can be associated with means, not shown, for generating air under pressure or suction to provide a difference in ambient pressure between the process compartment 4 and the collection receptacle 6. The resulting pressure difference is adapted to promote the transfer, through the riser channel 22, of the process waste from the process compartment 4 to the collection receptacle 6.

Moreover, the adjustment means 7 comprise a vent 26, which is connected to the collection receptacle 6, and a flow control valve 27, which is adapted to control the port 28 for connection between the riser duct 19 and the supply duct 20 and the hole 29 defined within the stopper 3 for the passage of air from the intake port 23 to the containment chamber 5.

The valve 27 comprises a body which is associated so that it can rotate within a corresponding seat which is defined within the stopper 3 and in which there are a first radial notch 270, which is adapted to connect the first intake port 23 to the hole 29 for the inflow of air into the containment chamber 5, and a second radial notch 271, which is adapted to connect the riser duct 19 to the connecting port 28 which leads to the supply duct 20.

Figures 1, 2:
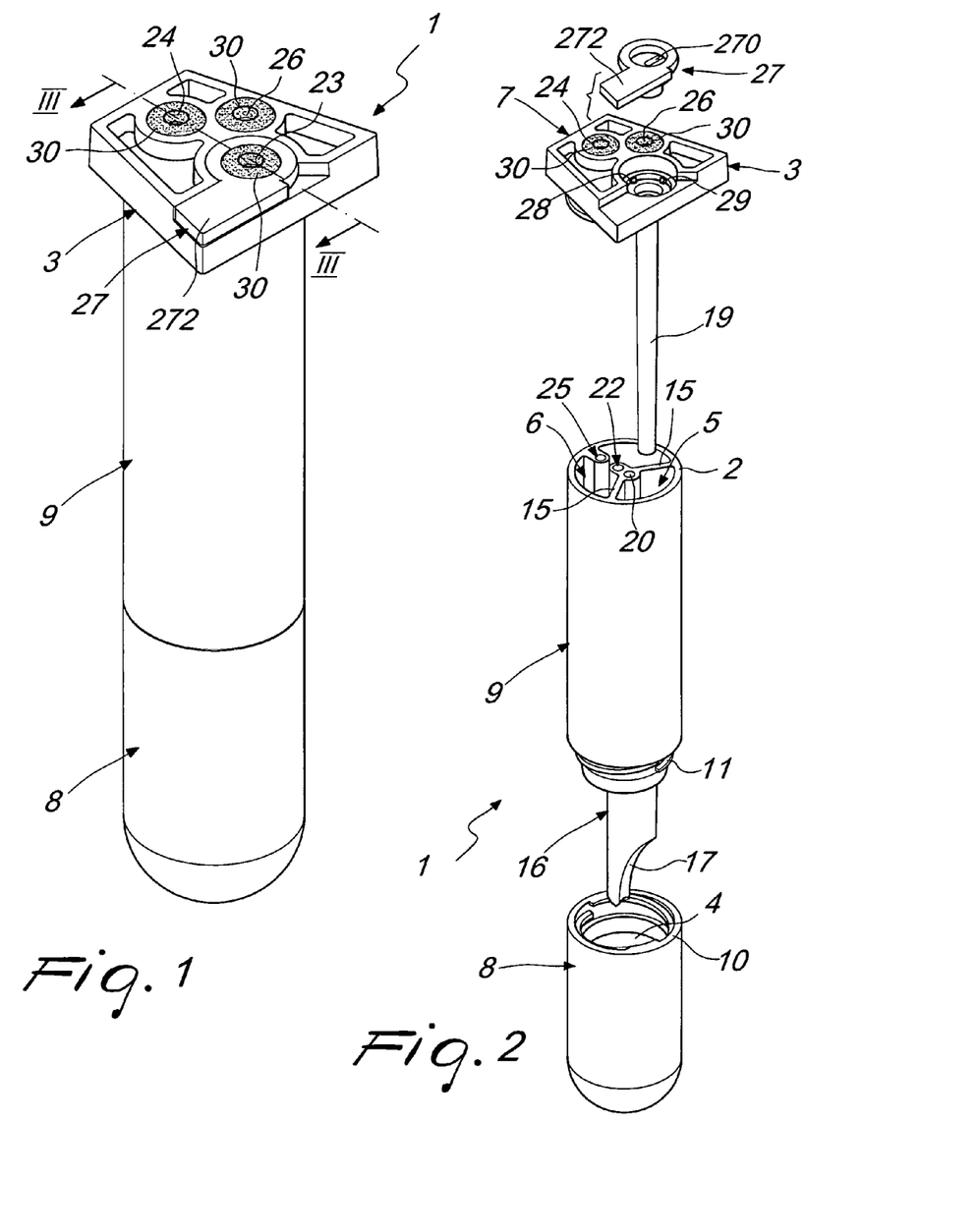
FIG. 1 is a perspective view of a reactor according to the invention.
FIG. 2 is an exploded view of FIG. 1.
Figures 3, 4:
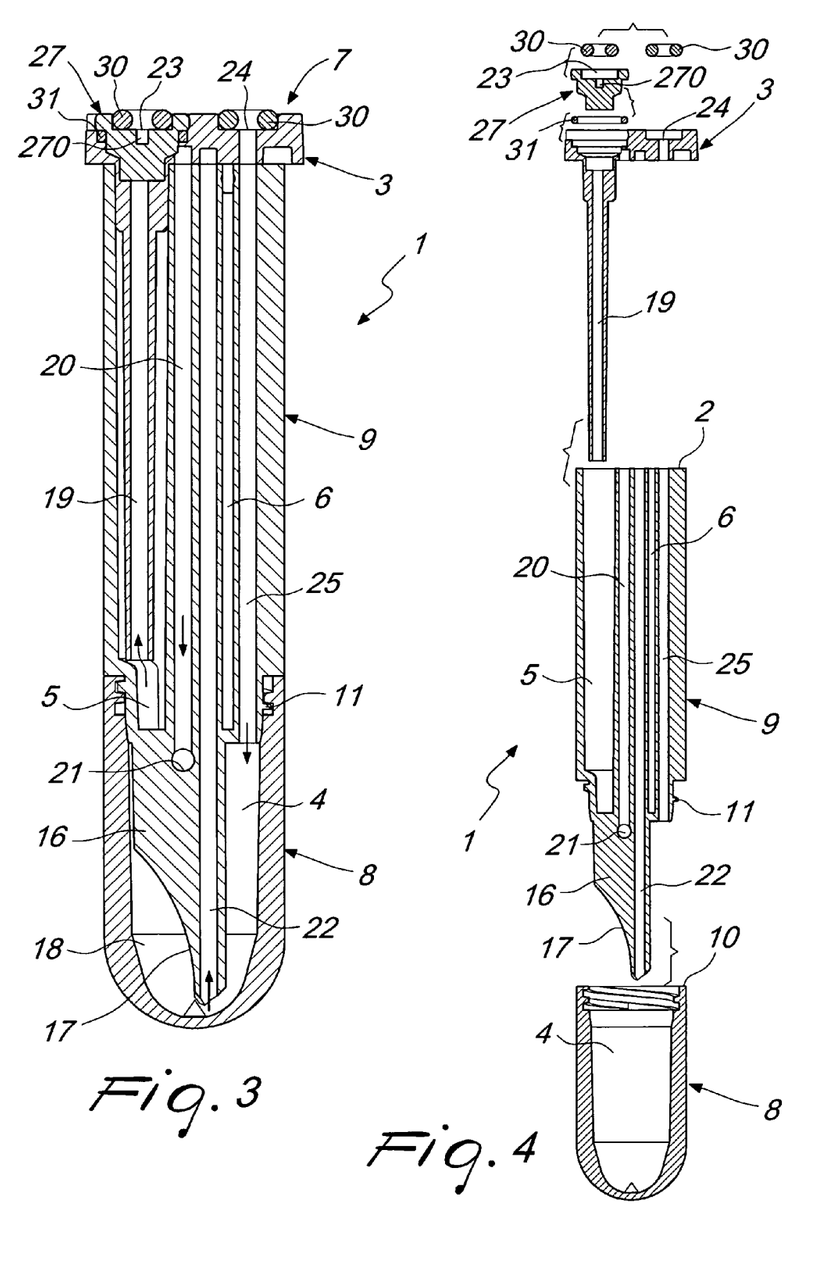
FIG. 3 is a sectional view, taken along the line III-III of FIG. 1.
FIG. 4 is an exploded view of FIG. 3.
Figures 5, 6:
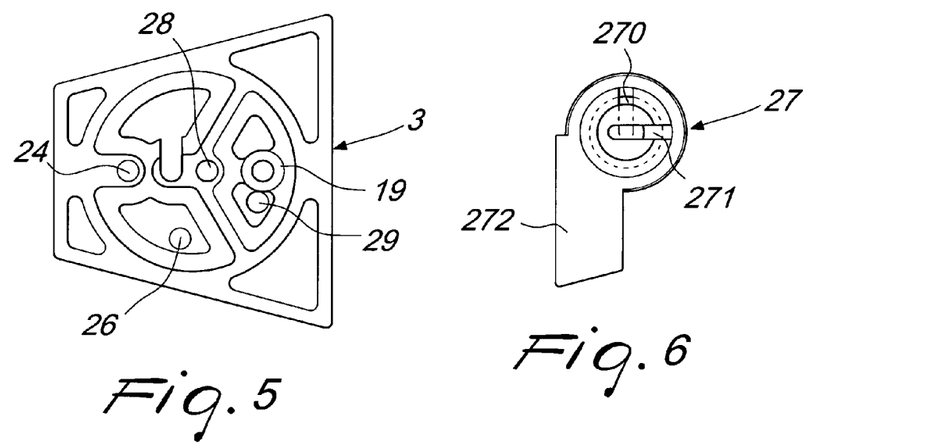
FIG. 5 is a bottom plan view of the closure means of the reactor according to the invention.
FIG. 6 is a bottom plan view of the valve for adjusting the first transfer means of the reactor according to the invention.
Figures 7, 8:
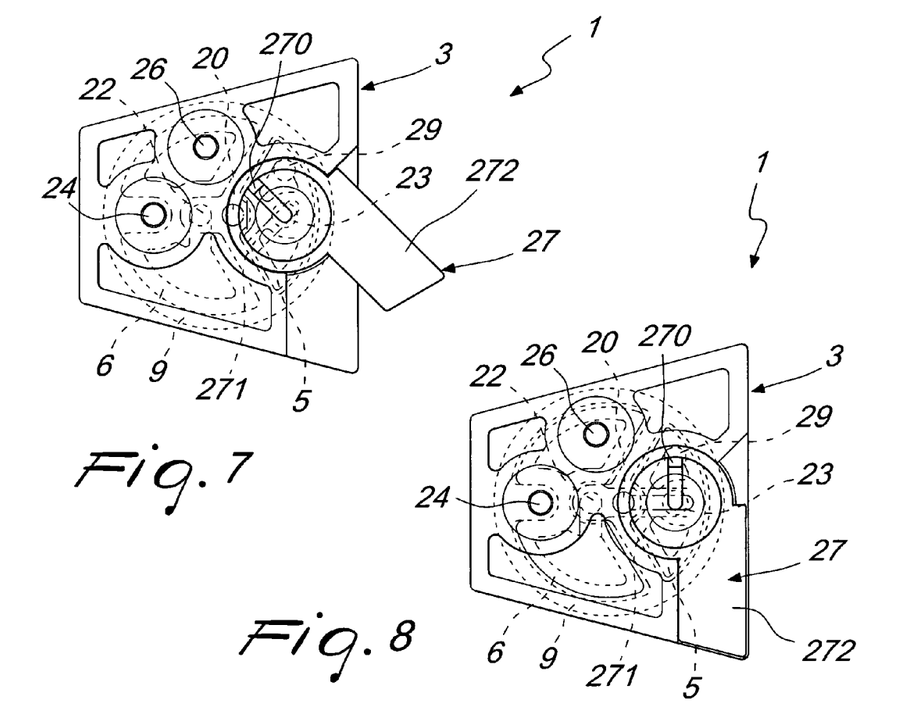
FIG. 7 is a top plan view of the reactor according to the invention, with the adjustment valve in the closed position.
FIG. 8 is a top plan view of the reactor according to the invention, with the adjustment valve in the open position.
Figures 9, 10:
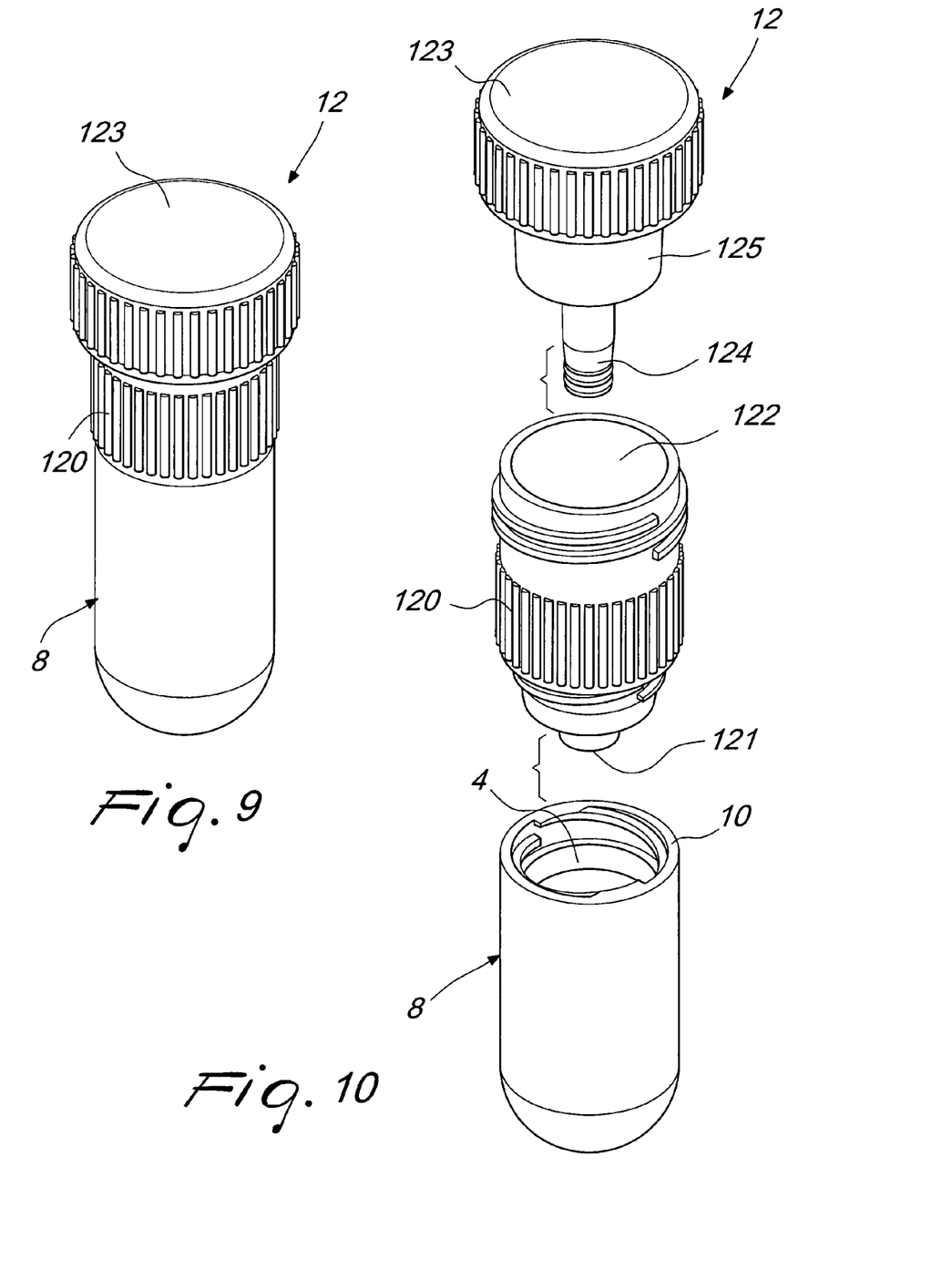
FIG. 9 is a perspective view of the capsule of the reactor according to the invention in the closed condition.
FIG. 10 is an exploded view of FIG. 9.
Figures 11, 12:
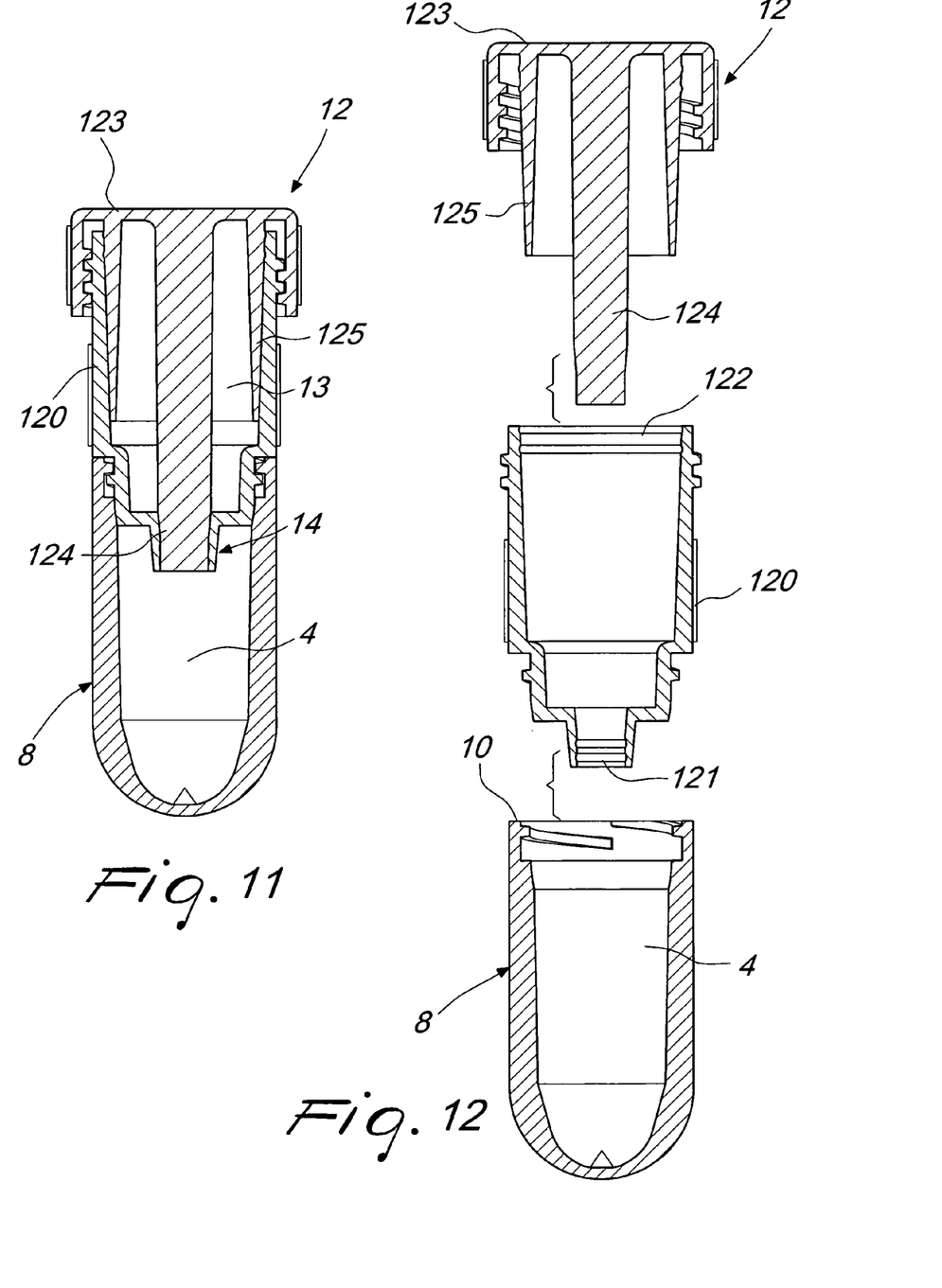
FIG. 11 is an axial sectional view of FIG. 9.
FIG. 12 is an exploded view of FIG. 11.

The valve 27 is further provided with an actuation lever 272; in FIGS. 7 and 8, the reactor 1 is shown with the valve 27 in the two closed and open positions.

Respective sealing gaskets 30 are arranged at the intake ports 23 and 24 and at the vent 26; likewise, a gasket 31 is interposed between the body of the valve 27 and the seat defined within the stopper 3.

FIGS. 9-12 illustrate the capsule 8 provided with the closure element 12.

The closure element 12 comprises a hollow body 120, which is associated with the upper opening 10 of the capsule 8 and is provided with a first open end 121, which protrudes into the process compartment 4, and with a second open end 122, which protrudes outside the process compartment 4.

Moreover, the closure element 12 comprises a lid 123 for temporarily closing the second end 122 and from which a plug 124 for closing the first end 121 and a tubular jacket 125 which is coaxial thereto protrude.

The space 13 remains formed between the hollow body 120 and the lid 123, which are coupled to each other, while the transfer means 14 are formed by the first end 121 once the lid 123, and therefore the plug 124, has been removed.

The reactor 1 is made of a polymeric material of the thermoplastic type, selected from the group which comprises: polyethylene (PE), high-density polyethylene (PEHD) and polypropylene (PP).

With particular reference to processes for extracting and purifying nucleic acids (DNA, RNA), it has in fact been found experimentally that pellets of these acids adhere strongly to these materials.

The reactor 1 is prepared as follows:
first of all, the closure element 12 is prepared: the lid 123 is
overturned so that the tubular jacket 125 acts as a cup, into which a process agent is introduced which, in the case of processes for extracting nucleic acids, is constituted by isopropyl alcohol; the hollow body 120 is screwed to the lid 123 and the plug 124 enters the first open end 121; the resulting assembly forms the closure element 12, which is associated with the capsule 8 within which another process agent has been introduced; in the case of a biochemical process for extracting and purifying nucleic acids, said agent is constituted by a lysis agent.

The containment chamber 5 is prefilled with a respective process agent, which, in the case of a biochemical process for extracting and purifying nucleic acids, is constituted by a washing agent such as 70% ethanol. The tubular body 9 is then closed by the stopper 3 with the valve 27 in the closed position.

Operation of the reactor according to the invention is now described with reference to a process for extracting and purifying nucleic acid from a biochemical sample according to the present invention, the use of the reactor according to the invention not being limited to this process.

The process for extracting and purifying nucleic acid according to the invention comprises the following steps:

a) providing a reactor 1 made of PP or PEHD and in which the capsule 8 is separated from the tubular body 9. The capsule 8 is prefilled with a lysis agent and is closed by the closure element 12, the space 13 of which contains isopropyl alcohol. The tubular body 9 is closed by the stopper 3 and the containment chamber 5 is prefilled with a washing agent.

b) removing the lid 123 from the capsule 8; in this way, the plug 124 frees the first open end 121 through which the isopropyl alcohol pours into the process compartment 4, where it mixes with the lysis agent.

c) introducing in the process compartment 4 the biochemical sample to be processed, such as for example human plasma or serum, physiological liquids, human and nonhuman cells, bacterial colonies, tissue homogenates.

d) coupling the capsule 8 to the lower end 11 of the tubular body 9.

e) by acting on the valve 27, connecting the riser duct 19 to the supply duct 20 and the first intake port 23 to the air intake hole 29 in the containment chamber 5.

f) subjecting the reactor 1 thus assembled to a first centrifugation, until pellets of nucleic acid separate which adhere to the internal surface of the process compartment 4 proximate to the accumulation region 18 and supernatant waste forms.

g) actuating the means 7 for adjusting the second transfer means in order to transfer the supernatant process waste from the process compartment 4 to the collection receptacle 6. In detail, through the second intake port 24 and the duct 25, a positive pressure differential is generated between the process compartment 4 and the collection receptacle 6, so as to trigger the flow of the supernatant from the intake hole along the riser channel 22 to the discharge hole which leads into the receptacle 6.

h) actuating the adjustment means 7 of the first transfer means to transfer the washing agent from the containment chamber 5 to the process compartment 4. In detail, air is introduced through the first intake port 23 and the hole 29 so as to generate a positive pressure difference between the containment chamber 5 and the process compartment 4. In this manner, the flow of the washing agent, along the riser duct 19 to the discharge end 21 which introduces it into the process compartment 4, is primed.

i) subjecting the reactor 1 to a second centrifugation.

l) actuating the adjustment means of the second transfer means to transfer the exhausted washing agent from the process compartment 4 to the collection receptacle 6 as in step g). The pellet of purified nucleic acid remains adhered to the internal surface of the process compartment 4.

m) removing the capsule 8, which contains the pellet of separated and purified nucleic acid, from the tubular body 9 to recover the pellet, the tubular body 9 constituting waste material.

The lysis agent comprises guanidine isothiocyanate, the process agent contained in the compartment of the closure element 12 is isopropyl alcohol, and the washing agent is 70% ethanol.

The first centrifugation occurs at 14,000 rpm for 10 minutes, while the second centrifugation occurs at 14,000 rpm for 5 minutes.

Figure 13:
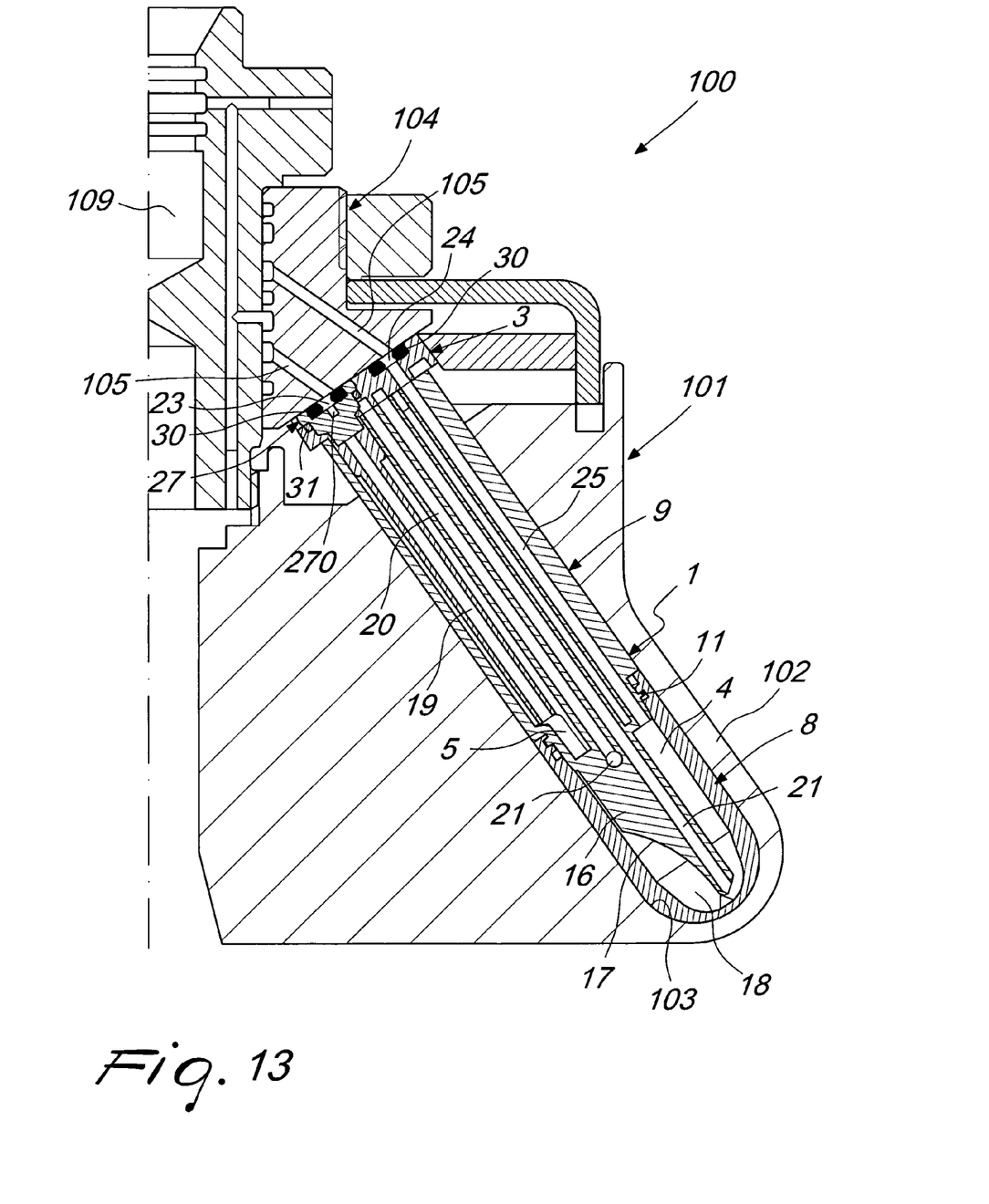
FIG. 13 is a schematic sectional view of a portion of a centrifugation apparatus according to the invention.
Figure 14:
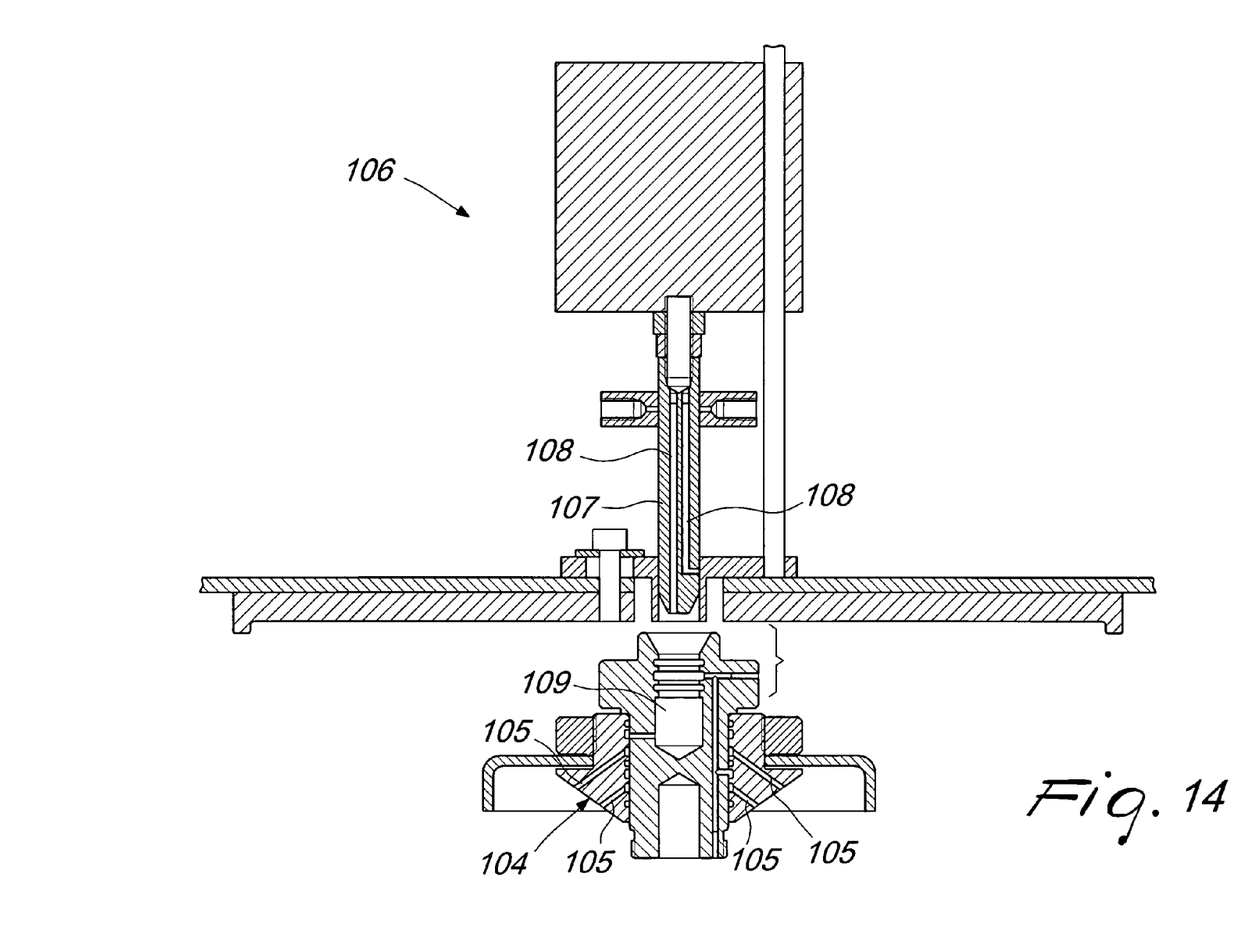
FIG. 14 is a schematic sectional view of a detail of the centrifugation apparatus according to the invention.

FIGS. 13 and 14 partially illustrate an apparatus 100 for the automated execution of biochemical processes by using reactors 1 which provide at least one centrifugation step.

The apparatus 100 comprises a centrifugation device 101 which is provided with a rotor 102 in which one or more receptacles 103 are provided for a respective reactor 1 which is inclined by a fixed angle. A pneumatic distribution unit 104 is associated in axial alignment with the rotor 102 and is provided, for each reactor 1, with two paths 105, which can be connected in input to means 106 for generating air under pressure and in output to the intake ports 23 and 24 of the first and second transfer means of each reactor 1.

The means 106 for generating air under pressure comprise a stem 107, in which one or more channels 108 for supplying air to the paths 105 are provided.

The stem 107 is supported above the rotor 102 and in axial alignment therewith so that it can move with a reciprocating rectilinear motion between an active configuration, in which it is inserted in a corresponding cavity 109 defined within the distribution unit 104 with the channels 108 connected to the respective paths 105, and an inactive configuration, in which it is extracted from the cavity 109.

Guiding means and linear actuation means for the reciprocating rectilinear motion of the stem 107 between the inactive configuration and the active configuration are provided.

There is also a control and actuation unit for driving the rotor 102 and the means 106 for generating air under pressure.

In particular, with reference to the biochemical process for extracting nucleic acids described above, after the first centrifugation, where the rotor 102 is stationary, the stem 107 is lowered into the active configuration until it enters the cavity 109.

Pressurized air is introduced through the channels 108 into the paths 105 which are connected to the second intake port 24; in this manner, an overpressure is created inside the process compartment 4 such as to facilitate the rise of the supernatants through the riser channel 22, which transfers them into the collection receptacle 6.

Subsequently, pressurized air is introduced through the channels 108 into the paths 105 which are connected to the first intake port 23; in this manner, the overpressure required to transfer the process agent from the containment chamber 5 to the process compartment 4 of each reactor 1 is generated.

The stem 107 is retracted into the inactive configuration and the second centrifugation is performed.

At the end of the second centrifugation, the stem 107 is lowered again into the active configuration to transfer the exhausted process agent from the process compartment 4 to the collection receptacle 6.

Finally, the stem 107 is lifted again and the reactors 1 are extracted from the apparatus 100.

It is found that with the apparatus according to the invention the entire biochemical process is performed without the need to remove the reactor or reactors from the centrifugation device 101.

The reactor according to the invention is of the disposable type and is adapted to process biochemical samples of different volumes, typically from 100 µl to 5 ml, particularly 200 µl.

In practice it has been found that the described invention achieves the proposed aim and objects.

Since the reactor according to the invention can be prefilled with process agents, it allows to perform biochemical processes simply and easily without the need to perform subsequent operations for opening and closing it, to the advantage of operator safety.

Since the reactor according to the invention can be prefilled, it allows to automate easily the steps in which a biochemical process is performed with the use of tools which have a simple structure and low installation and management costs.

The reactor according to the invention, particularly in the first embodiment, allows to perform biochemical processes which provide for at least one centrifugation step without the need to remove such reactor from the centrifugation device.

The process according to the invention allows to process biochemical samples of any volume, typically ranging from 100 µl to 5 ml, particularly 200 µl, and to extract, by way of the adhesion of the nucleic acid pellet to the PP or PEHD walls, all of the nucleic acid that is present in the processed sample.

The invention thus conceived is susceptible of numerous modifications and variations, all of which are within the scope of the appended claims.

All the details may further be replaced with other technically equivalent ones.

In practice, the materials used, as well as the shapes and dimensions, may be any according to requirements without thereby abandoning the scope of the protection of the appended claims.

The disclosure in Italian Patent Application No. MI2006A002272 from which this application claims priority are incorporated herein by reference.

Where technical features mentioned in any claim are followed by reference signs, those reference signs have been included for the sole purpose of increasing the intelligibility of the claims and accordingly, such reference signs do not have any limiting effect on the interpretation of each element identified by way of example by such reference signs.

The invention claimed is:

1. A reactor for performing biochemical processes, for extraction, purification, enrichment, sedimentation, characterized in that it comprises a container which is provided with at least one mouth which is associated with closure means of the removable type, said container having internally at least one process compartment, adapted to accommodate a sample of biochemical material to be processed, at least one containment chamber for a process agent, and at least a first means for transferring said process agent from said containment chamber to said process compartment;

wherein said container comprises a capsule which is provided with an upper opening and inside which said process compartment is defined, and a tubular body which has an end which is detachably associated with said opening and the opposite end which is provided with said mouth, said containment chamber and said first transfer means being defined within said tubular body.

2. The reactor according to claim 1, characterized in that it comprises a plurality of said containment chambers and a plurality of said first transfer means.

3. The reactor according to claim 1, characterized in that at least one collection receptacle for collecting process waste and a second transfer means for transferring waste from said process compartment to said collection receptacle are defined inside said container.

4. The reactor according to claim 3, characterized in that it comprises means for adjusting said first transfer means and/or said second transfer means which are associated with said closure means and can be actuated from outside.

5. The reactor according to claim 3, characterized in that said collection receptacle and said second transfer means are defined within said tubular body.

6. The reactor according to claim 1, characterized in that it comprises a closure element of the removable type for said upper opening, said capsule being separate with respect to said tubular body.

7. The reactor according to claim 6, characterized in that said closure element comprises at least one space for containing a process agent, means for transferring said process agent from said containment space to said process compartment being provided.

8. The reactor according to claim 7, characterized in that said closure element comprises a hollow body which is associated with said upper opening of the capsule and is provided with a first open end which protrudes into said process compartment and with a second open end which protrudes outside said process compartment, and a lid for temporarily closing said second end from which a plug for closing said first end and a tubular jacket protrude, said space being defined between said hollow body and said lid which are mutually coupled and said transfer means being defined by said first open end.

9. The reactor according to claim 1, characterized in that said first transfer means comprise at least one riser duct for the rise of said agent which is provided, at one end, with an intake orifice which is accommodated within said containment chamber and, at the opposite end, with a discharge orifice which is connected to said process compartment.

10. The reactor according to claim 9, characterized in that said first transfer means comprise a duct for supplying said agent which has an intake end connected to said discharge orifice and a discharge end which leads into said process compartment.

11. The reactor according to claim 3, characterized in that said second transfer means comprise at least one channel for the rise of said waste which is provided, at one end, with an intake hole which is accommodated within said process compartment and, at the opposite end, with a discharge hole which is connected to said collection receptacle.

12. The reactor according to claim 9, characterized in that said riser duct is of the capillary type.

13. The reactor according to claim 4, characterized in that said adjustment means comprise at least one intake port, which is defined within said closure means and can be associated with means for generating pressurized air or suction and is connected to said containment chamber or to said process compartment in order to generate a difference in ambient pressure respectively between said containment chamber and said process compartment, for the transfer of said agent, or between said process compartment and said collection receptacle, for the transfer of said waste.

14. The reactor according to claim 13, characterized in that said adjustment means comprise at least one vent which is defined within said closure means and is connected to said collection receptacle.

15. The reactor according to claim 13, characterized in that said adjustment means comprise a valve for controlling the flow of said first transfer means.

16. The reactor according to claim 1, characterized in that said tubular body is provided, at said end thereof associated with the upper opening of said capsule, with a tab which protrudes into said process compartment and has an at least partially arc-like edge which delimits, in cooperation with the internal surface of said process compartment, a region for the accumulation of the process products.

17. The reactor according to claim 1, characterized in that it is made of thermoplastic material selected from the group consisting of: polyethylene (PE), high-density polyethylene (PEHD), and polypropylene (PP).

18. The reactor according to claim 4, characterized in that said process compartment and/or said containment chamber are prefilled with a respective process agent.

19. The reactor according to claim 18 for biochemical processes for extracting and purifying nucleic acid from a biochemical sample, characterized in that said process compartment is prefilled with a lysis agent and in that it comprises a containment chamber which is prefilled with a washing agent.

20. A biochemical process for extracting and purifying nucleic acid by using the reactor according to claim 19, comprising:
   introduction of said biochemical sample in said process compartment;
   a first centrifugation of the reactor until a pellet of nucleic acid adhered to the internal surface of said process compartment is separated;
   actuation of said means for adjusting the second transfer means in order to transfer the supernatant process waste from said process compartment to said collection receptacle;
   actuation of said adjustment means of said first transfer means for the transfer of said washing agent from said containment chamber to said process compartment;
   a second centrifugation of the reactor;
   actuation of said adjustment means of said second transfer means for transfer of exhausted washing agent from said process compartment to said collection receptacle, the pellet of purified nucleic acid adhering to the internal surface of said process compartment.

21. The process according to claim 20, comprising removing said capsule from said tubular body to recover said pellet of purified nucleic acid from said process compartment.

22. The process according to claim 20, wherein said sample is inserted in said capsule, said capsule being separated from said tubular body and being associated with said tubular body once insertion has occurred.

23. The process according to claim 20, wherein said lysis agent comprises a mixture of guanidine isothiocyanate and isopropyl alcohol.

24. The process according to claim 20, wherein said washing agent comprises 70% ethanol.

25. The process according to claim 20, wherein said first centrifugation occurs at 14,000-16,000 rpm for 10 minutes.

26. The process according to claim 20, wherein said second centrifugation occurs at 14,000-16,000 rpm for 5 minutes.

27. An apparatus for performing biochemical processes with a reactor according to claim 3, wherein said apparatus comprises a centrifugation device which is provided with a rotor in which there is at least one receptacle for a reactor and with which a pneumatic distribution unit is associated which is provided with one or more paths which can be connected in input to means for generating pressurized air or suction and in output to at least one of said first transfer means and said second transfer means of said reactor.

28. The apparatus according to claim 27, characterized in that said means for generating air under pressure or suction comprise a stem in which one or more channels for supplying air to said paths of said distribution unit are provided and which is supported above said rotor so that it can move with a reciprocating rectilinear motion between an active configuration, in which it is inserted in a corresponding cavity defined in said distribution unit with said supply channels connected to the respective paths, and an inactive configuration, in which it is extracted from said cavity.

29. The apparatus according to claim 28, characterized in that it comprises means for the linear actuation of the reciprocating rectilinear motion of said stem.

30. The apparatus according to claim 27, characterized in that it comprises a control and actuation unit for driving said rotor and said means for generating pressurized air or suction.

* * * * *